United States Patent
Yadav et al.

(10) Patent No.: US 12,390,797 B2
(45) Date of Patent: Aug. 19, 2025

(54) CATALYST FOR CO2 METHANATION REACTION HAVING HIGH ACTIVITY AND LONG TERM STABILITY AND PROCESS THEREOF

(71) Applicants: Institute of Chemical Technology, Mumbai (IN); ONGC Energy Centre Trust, Laxmi Nagar (IN)

(72) Inventors: Ganapati Dadasaheb Yadav, Mumbai (IN); Ashish Dilip Shejale, Mumbai (IN); Radhika Sadashiv Malkar, Mumbai (IN); Sanjeev Katti, Laxmi Nagar (IN); Damaraju Parvatalu, Laxmi Nagar (IN)

(73) Assignees: ONGC ENERGY CENTRE TRUST, Laxmi Nagar (IN); INSTITUTE OF CHEMICAL TECHNOLOGY, Mumbai (IN)

( * ) Notice: Subject to any disclaimer, the term of this patent is extended or adjusted under 35 U.S.C. 154(b) by 364 days.

(21) Appl. No.: 17/796,068

(22) PCT Filed: Jan. 21, 2021

(86) PCT No.: PCT/IN2021/050061
§ 371 (c)(1),
(2) Date: Jul. 28, 2022

(87) PCT Pub. No.: WO2021/152614
PCT Pub. Date: Aug. 5, 2021

(65) Prior Publication Data
US 2023/0108996 A1    Apr. 6, 2023

(30) Foreign Application Priority Data
Jan. 31, 2020    (IN) .............................. 202021004464

(51) Int. Cl.
*B01J 23/78* (2006.01)
*B01J 23/10* (2006.01)
(Continued)

(52) U.S. Cl.
CPC ............... *B01J 23/78* (2013.01); *B01J 23/10* (2013.01); *B01J 23/755* (2013.01); *B01J 35/615* (2024.01);
(Continued)

(58) Field of Classification Search
CPC . B01J 23/04; B01J 23/78; B01J 35/647; B01J 35/615; B01J 35/635; B01J 35/638;
(Continued)

(56) References Cited

U.S. PATENT DOCUMENTS 4,476,246 A * 10/1984 Kim ..................... B01D 53/945
423/213.5
4,780,447 A * 10/1988 Kim ....................... B01J 23/894
502/303
7,632,778 B2 * 12/2009 Wanninger ........... B01J 19/0013
502/344

FOREIGN PATENT DOCUMENTS

CN          103084174 A     5/2013
EP          2776164 A1      9/2014
(Continued)

OTHER PUBLICATIONS

International Search Report and Written Opinion of the International Searching Authority for PCT/IN2021/050061, dated Mar. 18, 2021.
(Continued)

*Primary Examiner* — Patricia L. Hailey
(74) *Attorney, Agent, or Firm* — Troutman Pepper Locke LLP (57) ABSTRACT
The present invention relates to a novel heterogeneous catalyst for selective carbon dioxide methanation reaction
(Continued)

having high activity and long-term stability, wherein the catalyst comprising of at least one alkali promoter metal, active metals selected from Nickel and Iron and a stable support for active metals having combination of $CeO_2$-$\gamma Al_2O_3$. Further, the present invention provides a process for synthesis of said catalyst. Secondly, the present invention also provides a sustainable process for synthesis of methane using said novel heterogenous catalyst. The benefits of present invention are that it provides a sustainable $CO_2$ methanation process as the novel outstanding catalyst having high performance and long-term stability and totally eliminates catalyst regeneration or reloading step due to its very long-term stability for >1000 h.

7 Claims, 9 Drawing Sheets

(51) Int. Cl.
| | |
|---|---|
| *B01J 23/755* | (2006.01) |
| *B01J 35/61* | (2024.01) |
| *B01J 35/63* | (2024.01) |
| *B01J 35/64* | (2024.01) |
| *B01J 37/00* | (2006.01) |
| *B01J 37/02* | (2006.01) |
| *B01J 37/03* | (2006.01) |
| *B01J 37/04* | (2006.01) |
| *B01J 37/06* | (2006.01) |
| *B01J 37/08* | (2006.01) |
| *C07C 1/12* | (2006.01) |

(52) U.S. Cl.
CPC ............ *B01J 35/617* (2024.01); *B01J 35/635* (2024.01); *B01J 35/638* (2024.01); *B01J 35/647* (2024.01); *B01J 37/009* (2013.01); *B01J 37/0236* (2013.01); *B01J 37/035* (2013.01); *B01J 37/04* (2013.01); *B01J 37/06* (2013.01); *B01J 37/08* (2013.01); *C07C 1/12* (2013.01); *C07C 2523/78* (2013.01)

(58) Field of Classification Search
CPC ........ B01J 35/617; B01J 23/10; B01J 23/755; B01J 37/009; B01J 37/0236; B01J 37/035; B01J 37/04; B01J 37/06; B01J 37/08; C07C 1/12; C07C 2523/78
USPC .................. 502/304, 330, 335–338; 423/628
See application file for complete search history.

(56) References Cited

FOREIGN PATENT DOCUMENTS

| | | | |
|---|---|---|---|
| KR | 1020140087264 A | 7/2014 | |
| WO | WO-2008127492 A2 * | 10/2008 | ............... B01J 23/60 |

OTHER PUBLICATIONS

Mutschler et al: "CO2 hydrogenation reaction over pristine Fe, Co, Ni, Cu and Al2O3 supported Ru: Comparison and determination of the activation energies", Oct. 2 018, Journal of Catalysis, 366:139-149. DOI: 10.1016/j.jcat.2018.08.002 pp. 139-149.

R. Meshkini et al: "Catalytic Properties of Ni—Fe Systems in the Reaction of co 2 Methanation at Atmospheric Pressure", Jun. 2017, Acta Physica Polonica A; 133(4), 1088-1090, DOI: 10.12693/APhysPolA.133.1088 pp. 1088-1090.

Salvatore Abate et al: "Catalytic Performance of Al2O3—ZrO2—TiO2—CeO2 Composite Oxide Supported Ni- based Catalysts for CO2 Methanation" Mar. 2016, Industrial & Engineering Chemistry Research 55(16), DOI: 10.1021/acs.iecr.6b00134 p. 1-27.

* cited by examiner

CATALYST FOR CO2 METHANATION REACTION HAVING HIGH ACTIVITY AND LONG TERM STABILITY AND PROCESS THEREOF

This application is a national stage application under 35 U.S.C. § 371 of PCT Application No. PCT/IN2021/050061, filed 21 Jan. 2021, which claims the priority benefit of Indian Patent Application number 202021004464, filed 31 Jan. 2020.

FIELD OF INVENTION

The present invention relates to a heterogenous catalyst for methane production via $CO_2$ hydrogenation. More specifically, the present invention provides a novel heterogeneous catalyst-support system having high activity and selectivity along with long term stability for continuous methane production through $CO_2$ methanation process for more than 1000 hours (h). Further, the present invention provides a process for synthesis of said catalyst. Secondly, the present invention also provides a sustainable process of conversion of $CO_2$ into methane using said novel heterogeneous catalyst. The benefits of present invention are that it provides a sustainable $CO_2$ methanation process as the novel outstanding catalyst having high performance and long term stability and totally eliminates coke formation and catalyst regeneration or reloading step due to its very long term stability for >1000 h. This work is focused on direct hydrogenation of industrially produced greenhouse gasses like $CO_2$ to renewable fuel such as synthetic natural gas (SNG) by developing highly active and selective novel catalyst-support system in continuous fixed bed vapour phase reactor in order to control the global warming and related climate changes.

BACKGROUND OF THE INVENTION

Synthetic natural gas (SNG) is one of the promising energy carriers for the excessive electricity generated from variable renewable energy sources. Therefore, Methane (Synthetic natural gas) has become an important compound and playing important role in upgrading a power system based on renewable energy. Due to the fluctuating supply of wind and solar energy, storage systems are needed to stabilize the electricity grid. Synthetic natural gas (SNG) produced within the power-to-gas process is a promising and suitable chemical energy carrier due to its long-term storage ability and the existing infrastructure in the form of the natural gas grid. Therefore, a synthetic renewable methane, also referred as SNG (synthetic natural gas), can be injected into the existing gas network or stored and utilized on demand as fuel for transportation or for heating application or for power-to-gas application. SNG production from renewable $H_2$ and $CO_2$ via catalytic $CO_2$ methanation has gained much attention since $CO_2$ emissions could be simultaneously reduced. From last three decades, considerable efforts have been devoted to the application of CO and $CO_2$ methanation reactions for the production of SNG. The synthesis of $CH_4$ from $CO_2$ and renewable $H_2$ via the Sabatier reaction (Eq. 1) is a well-known process utilizing transition as well as noble based catalysts such as Ni, Fe, Co, etc. and Ru, Pt, Pd, Rh etc., respectively.
Overall Reaction (Eq. 1)

Many different metals such as Ni, Co, Fe, Cu, Ru, Rh, Ir, Pd, and Pt have been exploited as active metals in catalysts for CO and $CO_2$ methanation reaction. As discussed by Janna V. Veselovskay et. al in the paper "There are numerous catalysts composition reported for above said methanation process", a commercial granulated nickel methanation catalyst NKM-2V comprising the catalyst contains 23.4 wt. % of Ni, 13.3 wt. % of Al, 7.36 wt. % of Ca, 0.57 wt. % of Si is used for methanation process.

Martin et al. has shown $CeO_2$ supported metal catalyst gives maximum $CO_2$ conversion and methane production followed by $Al_2O_3$ supported catalysts. Whereas, because of the large metal particle sizes, silica has shown the lowest methane formation. Metal supported on MCM-41 and ZSM-5 gave poor $CO_2$ hydrogenation activity bellow 400° C. In the purification of natural gas, to remove the toxic impurities such as $CO_2$ and water.

Bakar and Toemen also studied methanation process in the presence of $H_2S$ gas using Pd/Ru/Ni (2:8:90)/$Al_2O_3$ catalyst. Maximum $CO_2$ conversion obtained without $H_2S$ was 52.95% at 400° C., which was later dropped to 35.03% with only 3.6% methane yield because of poisoning of the active sites by $H_2S$ gas. Hezhi Liu at. Al. in the publication "Effect of $CeO_2$ addition on Ni/$Al_2O_3$ catalysts for methanation of carbon dioxide with hydrogen", the Ni—$CeO_2$/$Al_2O_3$ catalysts with a nickel content of 15 wt % prepared via impregnating boehmite were found to be highly active and stable for methanation of carbon dioxide with hydrogen at a $H_2$/$CO_2$ molar ratio of 4. But the said catalyst fails to provide a stability for above 120 h.

Mutschler et al. have studied pristine metals such as Fe, Co, Ni, and Cu along with Ru/$Al_2O_3$. Among all CO and Ni pristine metals were found to be giving best selectivity for methane whereas Fe was more active towards CO formation. From above all comparison, they have concluded that Co, Ni and Ru/$Al_2O_3$ were most active for Sabatier reaction and Fe is active for reverse water gas shift reaction. A γ-$Al_2O_3$ is the widely studied support for methanation process but it shows limitations in the application because of its sintering issues.

Therefore, Mebrahtu et al. studied and found addition of a promoter such as mixed oxide to the γ-$Al_2O_3$ support, improved its efficiency. Nickel dispersed on ternary and quaternary mixed oxides of alumina-zirconia-titania-ceria catalyst was prepared and studied for $CO_2$ methanation. The final catalyst showed that the addition of promoter such as $CeO_2$ to 20% Ni/$Al_2O_3$—$ZrO_2$—$TiO_2$ leads to increase in catalytic efficiency. Ceria helps in keeping beta-type NiO species and improves its dispersion on support. An important study was performed by Le and co-workers for CO and $CO_2$ methanation over Ni/$CeO_2$ catalysts. It was found that the catalytic activity of this catalyst increased with the increase in surface area of $CeO_2$ support. Larger dispersion of Ni and strong $CO_2$ adsorption over $CeO_2$ support led to the maximum activity of the catalyst for $CO_2$ methanation reaction.

Nevertheless, the currently reported catalysts are providing acceptable activity and selectivity for $CO_2$ methanation reaction, the main concern of prior art catalysts for industrial applications is catalyst deactivation, possibly due to metal sintering and/or carbon formation. Because, along with the main $CO_2$ methanation reaction (Eq. 1), six other side reactions can simultaneously occur depending upon the catalyst used. These side-reactions are as follows:
(i) Reverse Water-Gas-Shift (RWGS)

(Eq. 2)

(ii) CO Hydrogenation $$CO+3H_2 \leftrightarrow CH_4+H_2O, \Delta H°_{298K}=-206.1 \text{ kJ mol}^{-1} \quad \text{(Eq. 3)}$$

(iii) Water-Gas Shift Reaction (WGS)

$$CO+H_2O \leftrightarrow CO_2+H_2, \Delta H°_{298K}=-41 \text{ kJ mol}^{-1} \quad \text{(Eq. 4)}$$

(iv) Boudouard Reaction (BR)

$$2CO \rightarrow CO_2+C, \Delta H°_{298K}=-171 \text{ kJ/mol} \quad \text{(Eq. 5)}$$

(v) $CO_2$ Hydrogenation $$CO_2+2H_2 \leftrightarrow C+2H_2O, \Delta H°_{298K}=-90.147 \text{ kJ mol}^{-1} \quad \text{(Eq. 6)}$$

(vi) Methane Decomposition (MD)

$$CH_4 \leftrightarrow C+2H_2, \Delta H°_{298K}=74.8 \text{ kJ mol}^{-1} \quad \text{(Eq. 7)}$$

As represented in Eq. 1, $CO_2$ methanation is a highly exothermic reaction. However, it is difficult to proceed because of the high kinetic barriers of the eight-electron reduction process. This process is conducted starting from $CO_2$ and $H_2$ raw materials with six kinds of products such as $CO_2$, CO, $H_2$, $CH_4$, $H_2O$ and C deposit are possible (possibly through Eq. 2 to 7). There are four independent reactions for methanation process, as listed in Eq. (3-6).

From the perspective of thermodynamic equilibrium, in order to gain a better $CH_4$ yield from $CO_2$ and $H_2$, the reaction pathways of Eqs. 2 and 3 should be avoided. Hydrogenation of $CO_2$ to CO also called as reverse water-gas shift (RWGS) reaction (Eq. 2) acts as an important intermediate step in the Sabatier reaction. Thus, formed CO from this reaction is an unwanted product in $CO_2$ methanation process (Eq. 2). It can further lead to the deactivation of catalyst.

The foregoing analysis of the literature reveals that all the catalysts developed so far are successful in giving good yield and selectivity for methane but still there they lack in providing increase in the conversion of $CO_2$ at lower temperature with avoiding carbon formation on catalyst bed and thereby providing long term stability to catalyst in terms of time on stream study. Therefore, the effective catalyst provided in literature results in the inactive catalyst after some process cycles. The presence of hydrocarbons in the feed or during the reaction process has been found to enhance the formation of carbon species at the surface, which lead either to encapsulation or detachment of metal particle from catalyst's surface and to its progressive deactivation. Therefore, the challenges of providing long term stable catalyst for methanation process remains in the prior art.

Hence, as per objective of present invention, the inventors of present invention have developed a catalyst for complete conversion of intermediate CO using novel catalyst system which can operate at lower temperature, highly selective towards $CH_4$ and stable at all practical operating conditions. Therefore, the long-term stable catalyst and long term active catalyst with efficient conversion of methane makes the more efficient and sustainable methanation process.

Hence, the inventors of the present invention provides a heterogeneous catalyst having long term stability, very high catalytic activity and selectivity for $CO_2$ methanation process condition without production of coke and thereby provides a sustainable methanation process without need of regeneration step for more than 1000 h. The present invention provides a novel catalyst for $CO_2$ methanation comprising of active metals selected from nickel and iron and stabilising metal cesium, all supported on combination of $CeO_2$-$\gamma Al_2O_3$. The present invention also provides cost efficient process to prepare the said catalyst.

Therefore, the present invention of catalysts along with specific active metals, stabilising metal and support is developed to ensure high activity and selectivity along with long term stability (>1000 h), minimal by-products, no coke formation.

OBJECTIVES OF THE INVENTION

The primary objective of the present invention aims for design and development of highly active, selective, very stable (>1000 h) and robust catalyst-support system for $CO_2$ methanation process.

Second objective of the present invention is providing a sustainable process for $CO_2$ methanation reaction in order to control the global warming and related climate changes.

Yet another objective of the present invention is to provide heterogeneous $CO_2$ methanation catalyst that providing a high reactant conversion and selectivity at preferred temperature, no coke formation, resistance against metal sintering, high thermal stability for longer period of time for more than 1000 h.

SUMMARY OF THE INVENTION

The present invention relates to a heterogenous catalyst for methane production via $CO_2$ hydrogenation. More preferably, the present invention provides a heterogeneous catalyst for selective carbon dioxide methanation reaction having high activity and long-term stability (>1000 hours), the catalyst comprising of at least one alkali promoter metal, two active metals and support for active metals having combination of $CeO_2$-$\gamma Al_2O_3$ in mole ratio of 3:2; catalyst was synthesized and characterized in such a way that it is having surface area between 200 and 800 (m²/g), pore volume between 0.5 and 2.5 (cm³/g) and average pore diameter between 5 and 30 nm.

In accordance to present invention, the present invention provides a heterogeneous catalyst for selective carbon dioxide methanation reaction comprising of Cesium as alkali promoter and the concentration of Cesium is between 1 and 5 wt. % on the basis of total weight of the support.

Further, the active metals for carbon dioxide methanation reaction combination of Nickel and Iron and the said combination of metals are present in catalyst between 5 and 20 wt. % on basis of total weight of the support combination.

In accordance to second embodiment, the present invention provides a process for preparation of heterogeneous catalyst for selective carbon dioxide methanation reaction is selected from hydrothermal-co-precipitation method, wherein the hydrothermal-co-precipitation method comprising of step:

Step 1) Drop-wise addition of nickel nitrate, iron nitrate and cesium nitrate to the aqueous solution mixture of cerium nitrate and aluminium nitrate at continuous stirring rate and temperature at 363 K, Step 2) Simultaneously, dropwise addition of $Na_2CO_3$ to the step 1) solution and maintaining alkaline pH between 9-10 by the addition of 2M NaOH solution, Step 3) Precipitating out the reaction mixture at 443 K for 24 h in Teflon lining bomb reactor (pressure vessel) for hydrothermal treatment, Step 4) Cooling the solution to room temperature and separation of precipitate by filtration, Step 5) Washing of precipitate with de-ionized water for several times to attain neutral pH, Step 6) Drying of precipitate at 383 K for 12 h, Step 7) Calcination of dried precipitate at temperature 973 K for 5 h in air atmosphere.

BRIEF DESCRIPTION OF DRAWINGS

For a more complete understanding of the features and advantages of the present invention, reference is now made to the detailed description of the invention along with the accompanying figures and in which.

DETAILED DESCRIPTION OF THE INVENTION

The present invention relates to a novel alkali promoted multifunctional heterogeneous catalyst for methane production via selective $CO_2$ hydrogenation comprising a stable support system of metal oxides having combination of basic metal oxide comprising $CeO_2$ and $\gamma Al_2O_3$, active metals selected from Nickel and iron and further comprising an alkali promoter. Further, the present invention also provides a preparation method of novel heterogeneous thereof, wherein the catalyst is prepared by hydrothermal co-precipitation method.

Surprisingly, it was found that the selective catalytic methanation catalyst for the treatment of an exhaust gas having $CO_2$ according to the present invention permits to improve the $CO_2$ conversion while preventing the carbon formation and deposition on catalyst bed for very longer time (more than 1000 h) under fix bed vapour phase reaction conditions leading to use the catalyst bed for longer duration of time without affecting feedstock conversion rate, product yield and therefore being cost effective.

The present invention also provides a process of synthesis of methane in presence of said novel heterogeneous and alkali promoted multifunctional catalyst, wherein the said catalyst performs a selective catalytic $CO_2$ methanation reaction in the fixed bed vapour phase reactor.

More preferably, the novel heterogeneous as provided in present invention is comprising of combination of cesium promoted nickel and iron active metals supported over $CeO_2$-$\gamma Al_2O_3$ support by using combination of the hydrothermal-co-precipitation technique. This new catalyst addressed all the possible difficulties associated with conventional catalyst-support combination for $CO_2$ methanation reaction. The combined $CeO_2$-$\gamma Al_2O_3$ support providing a stable support for active metals like nickel and iron having activity for methane production therefrom, which exhibiting a desirable balance of conversion rate from $CO_2$ to methane gas along with long term active stability of catalyst for sustainability in said production facility.

Hence, in accordance to an embodiment of the present invention, the said novel synthesized heterogeneous system i.e. Cs—Ni—Fe/$CeO_2$-$\gamma Al_2O_3$ has remained stable up to 1000 h which showed highest activity (85% $CO_2$ conversion and 84.2% $CH_4$ yield) and stability (99.5% $CH_4$ selectivity and 1000 h TOS) with no coke formation and has proven its efficacy for cost-effective and sustainable utilization of $CO_2$ to produce synthetic/substitute natural gas (SNG).

Accordingly, the present invention provides a long term stable and active catalyst for $CO_2$ methanation comprising of active metal selected from Nickel and Iron along with stabilising metal selected from cesium supported on stabilised support material selected from combination of $CeO_2$-$\gamma Al_2O_3$, wherein the said combination is selected between 1:1, 2:1, and 3:2 preferably 3:2 mole ratio.

Therefore, the present invention provides a novel catalyst composition for effective methanation process that is efficiently providing a high reactant conversion at given temperature ranging from 250 to 350° C. for longer time. More preferably the time of reaction that can be run with novel catalyst is more than 900 h, more preferably more than 1000 h. The said catalyst is active and physically stable without coke formation in the pore or upon the surface of catalyst also resistance against metal sintering, thereby catalyst deactivation gets inhibited.

In accordance an embodiment, the stable support of metal loading is combination of basic metal oxide is selected from 3:2 mole ratio. And basic metal oxide are selected from $CeO_2$ and $\gamma Al_2O_3$.

In accordance to one more embodiment, the active metals doped on said support is selected from combination of transition metals are selected form nickel and iron. In accordance to one of the embodiment, the percentage of said metals in said novel composition is ranging from 5 to 20 wt. % on basis of total weight of stable support combination ($CeO_2$-$\gamma Al_2O_3$). Wherein, the each metal concentration may vary from 5 to 20 wt. % on basis of total weight of stable support combination ($CeO_2$-$\gamma Al_2O_3$).

In accordance to one more embodiment, the said catalyst support system is stabilised by addition of cesium as alkali promoter metal in the said catalyst composition. The percentage of said alkali promoter metal in said novel composition is ranging between 1 and 5 wt. % on basis of total weight of stable support combination ($CeO_2$-$\gamma Al_2O_3$).

In accordance to one more embodiment, the present invention also provides a process to prepare the said long term active $CO_2$ methanation catalyst and sustainable process to prepare SNG using said long term active, selective, and stable catalyst.

The present invention is further described with the help of the following examples, which are given by way of illustration.

EXAMPLES

EXAMPLE 1: Catalysts synthesis: Several catalysts were synthesized and studied for $CO_2$ methanation reaction which have been divided into three sections, i.e. single metal oxides, mixed metal oxides, and alkali promoted mixed metal oxide.

A) Single metal Oxides: All single metal oxide catalysts, viz., $Ni/Al_2O_3$, $Ni/CeO_2$, $Ni/ZrO_2$, $Fe/Al_2O_3$, $Fe/CeO_2$, $Cu/Al_2O_3$ and $Cu/CeO_2$ have been synthesized by incipient wetness impregnation technique.

Method of synthesis by Incipient wetness impregnation technique: The monometallic Ni, Fe and Cu catalysts on different supports such as $Al_2O_3$, $CeO_2$, and $ZrO_2$ were prepared by incipient wetness impregnation technique to optimize the role of characteristics of different support on catalytic behaviour with an intended total metal loading of 10 wt. %. Calcination of the support materials ($Al_2O_3$, $CeO_2$, and $ZrO_2$) under air atmosphere was carried out before active metal (Ni, Fe and Cu) loading on the support. An aqueous solution of nickel, iron, and copper nitrate was utilized for the incipient wetness impregnation of Ni, Fe, and Cu catalysts (10 wt. %) over the above supports. In this method, impregnation was performed under continuous stirring of the solution for 24 h for complete pore filling. The addition was stopped on formation of sticky solid material. It was the time when the volume of adsorbed solution was the same as the pore volume of the support. Once the impregnation was complete and loading of 10 wt. % achieved, the material was dried at 383 K for 12 h and further calcined at 773 K for 3 h under air atmosphere. The calcined catalysts were further pressed, crushed and sieved to granules having size of 0.08e0.35 mm. Finally, all single metal oxide catalysts of 10 wt. % loading on support, viz., $Ni/Al_2O_3$, $Ni/CeO_2$, $Ni/ZrO_2$, $Fe/Al_2O_3$, $Fe/CeO_2$, $Cu/Al_2O_3$ and $Cu/CeO_2$ were kept ready to conduct $CO_2$ methanation reactions.

B) Mixed metal oxides: Different combinations of mixed metal oxide catalysts, viz., Ni—Fe/$CeO_2$—$Al_2O_3$, Ni—Cu/$CeO_2$—$Al_2O_3$, Ni—Fe/$CeO_2$—$ZrO_2$ and Ni—Cu/$CeO_2$—$ZrO_2$ catalysts were prepared by hydrothermal-co-precipitation method.

C) Alkali promoted mixed metal oxide: The alkali promoted multifunctional Cs—Ni—Fe/$CeO_2$-$\gamma Al_2O_3$ catalyst were prepared by hydrothermal-co-precipitation method as mentioned below.

Method of synthesis by Hydrothermal-co-precipitation technique: Different combinations of mixed metal oxide catalysts, viz., Ni—Fe/$CeO_2$—$Al_2O_3$, Ni—Cu/$CeO_2$—$Al_2O_3$, Ni—Fe/$CeO_2$—$ZrO_2$ and Ni—Cu/$CeO_2$—$ZrO_2$ as well as alkali promoted multifunctional Cs—Ni—Fe/$CeO_2$-$\gamma Al_2O_3$ catalyst were prepared by hydrothermal-co-precipitation method. All above mixed metal oxide catalysts except Cs—Ni—Fe/$CeO_2$-$\gamma Al_2O_3$ were prepared by maintaining Ce/Al mole ratio as 3:1. The mole ratio of Ce/Al for Cs—Ni—Fe/$CeO_2$-$\gamma Al_2O_3$ catalyst was maintained as 3:2. For the sake of illustration, preparation of Cs—Ni—Fe/$CeO_2$-$\gamma Al_2O_3$ catalyst via hydrothermal-co-precipitation technique is discussed further. The one pot synthesis of Cs promoted Ni—Fe/$CeO_2$—$Al_2O_3$ mixed oxide abbreviated as Cs—Ni—Fe/$CeO_2$-$\gamma Al_2O_3$ for conversion of $CO_2$ into synthetic natural gas (SNG) is as follows. This catalyst was synthesized by the combination of hydrothermal and co-precipitation (hydrothermal-co-precipitation) technique wherein, a mole ratio of support, viz., Ce/Al was maintained as 3:2. In this procedure, Ni (10 wt. %), Fe (10 wt. %), and Cs (5 wt. %) in the form of their nitrate salts were added drop-wise to the aqueous solution of support salts, i.e. Ce and Al nitrates; while maintaining continuous stirring at 363 K. Simultaneously, from an another end, dropwise addition of $Na_2CO_3$ was carried out for precipitation purpose. At the same time, alkaline pH of 9-10 was maintained throughout during the process by the addition of 2M NaOH solution. Such treatment of dropwise addition ensures uniform distribution of active metals in the lattice structure of the support. Later, the solution was transferred to a Teflon lining bomb reactor (pressure vessel) and kept at 443 K for precipitation (24 h), then allowed to cool naturally at room temperature. Next, the precipitate was filtered, washed with de-ionized water for several times to attain neutral pH and dried at 383 K for 12 h. The dried material was crushed to fine powder and further calcined at 973 K for 5 h in air atmosphere. Finally, the material was again crushed to fine powder and sieved to a fine particle size of 0.3-0.6 mm using a 30-60 size mesh to get novel catalyst viz., Cs promoted Ni—Fe/$CeO_2$—$Al_2O_3$ for $CO_2$ methanation reaction for higher activity, selectivity and stability.

D) Characterization of Catalysts by $N_2$ adsorption desorption data to determine BET surface area and porosity of Catalysts:

TABLE 1

BET surface area and porosity of catalysts

| Sr. No. | Catalyst | Mole ratio of support | Surface area ($cm^2/g$) | Pore volume ($cm^3/g$) | Average Pore diameter (nm) |
|---|---|---|---|---|---|
| 1 | Cs-Ni-Fe/$CeO_2$-$\gamma Al_2O_3$ | (Ce:$\gamma$Al - 3:2) | 477 | 1.9 | 20.2 |
| 2 | Cs-Ni-Fe/$CeO_2$-$\gamma Al_2O_3$ | (Ce:$\gamma$Al - 3:2) | 490 | 2.0 | 21.5 |
| 3 | Ni-Fe/$CeO_2$-$Al_2O_3$ | (Ce:Al - 3:2) | 383 | 1.7 | 17.6 |
| 4 | Ni-Fe/$CeO_2$-$Al_2O_3$ | (Ce:Al - 2:1) | 341 | 1.7 | 16.9 |
| 5 | Ni-Fe/$CeO_2$-$Al_2O_3$ | (Ce:Al - 1:1) | 336 | 1.6 | 16.4 |
| 6 | Ni-Fe/$CeO_2$-$Al_2O_3$ | (Ce:Al - 3:1) | 319 | 1.2 | 15.7 |
| 7 | Ni-Cu/$CeO_2$-$Al_2O_3$ | (Ce:Al - 3:1) | 307 | 1.2 | 15.5 |
| 8 | Ni-Fe/$CeO_2$-$ZrO_2$ | (Ce:Zr - 3:1) | 234 | 0.9 | 11.8 |
| 9 | Ni-Cu/$CeO_2$-$ZrO_2$ | (Ce:Zr - 3:1) | 192 | 0.8 | 10.4 |
| 10 | $Ni/Al_2O_3$ | — | 108 | 0.5 | 4.9 |
| 11 | $Fe/Al_2O_3$ | — | 97 | 0.5 | 4.3 |
| 12 | $Ni/CeO_2$ | — | 89 | 0.4 | 3.8 |
| 13 | $Fe/CeO_2$ | — | 77 | 0.4 | 3.8 |
| 14 | $Cu/Al_2O_3$ | — | 75 | 0.4 | 3.7 |
| 15 | $Cu/CeO_2$ | — | 66 | 0.3 | 3.5 |
| 16 | $Ni/ZrO_2$ | — | 43 | 0.2 | 2.6 |

EXAMPLE 2: Method of synthesis of Methane in presence heterogeneous catalyst via $CO_2$ Methanation Reaction using:

The catalysts prepared in example 1 including novel alkali promoted mixed metal oxides i.e Cs promoted Ni—Fe/$CeO_2$—$Al_2O_3$[Cs—Ni—Fe/$CeO_2$-$\gamma Al_2O_3$] was used for $CO_2$ methanation reaction.

A fixed bed vapour phase reactor (FBVPR) operated in down-flow mode having a length and internal diameter of 380 and 19 mm, respectively was used for experiments. All experiments were carried out under atmospheric pressure (0.1 MPa). The catalyst was first reduced (723 K) under the flow of hydrogen for 1 h at a fixed flow rate. Next, the mixture of $CO_2$ and $H_2$ in an appropriate mole ratio (1:4) was passed in the reactor through MFC at predetermined flow rate. The $CO_2$ and $H_2$ flow rate was adjusted to the desired value with an accuracy of ±1 $cm^3$/min. The temperature was controlled by using a temperature controller (West 6100b, Germany) having accuracy of ±1 K. A pressure transducer (range 0-50 MPa) measured pressure (uncertainty ±0.01 MPa). TCD and FID was used to analyze the gaseous and liquid products, respectively. Few experiments were replicated to ascertain the correctness of measurements (error ±2%).

TABLE 2

Details of Analytical technique

| Detector | Gas - Thermal Conductivity Detector (TCD) |  |  |
|---|---|---|---|
|  | Liquid - Flame Ionization Detector (FID) |  |  |
| Carrier Gas | Nitrogen |  |  |
| Column | Porapak Q (Gas) |  |  |
|  | Tenax TA(Liquid) |  |  |
| Temperature | Injector | Oven | Detector |
| (Gas) | 120° C. | 60° C. | 155° C. |
| Temperature | Injector | Oven | Detector |
| (Liquid) | 280° C. | 50° C. | 300° C. |

Wherein, the $CO_2$ conversion was defined as follows:

$$CO_2 \text{conversion (\%)} = \frac{[CO_2]_{in} - [CO_2]_{out}}{[CO_2]_{in}} * 100 \quad \text{Formula (1)}$$

where, $[CO_2]_{in}$ and $[CO_2]_{out}$ represent the inlet and outlet molar flow rate (mol $h^{-1}$) of $CO_2$.

The $CH_4$ yield was defined as follows:

$$CH_4 \text{yield (\%)} = \frac{[CH_4]_{out}}{[CO_2]_{in}} * \frac{5}{100} \quad \text{Formula (2)}$$

where, $[CH_4]_{out}$ represents the outlet molar flow rate (mol $h^{-1}$) of $CH_4$.

The Gas hourly space velocity (GHSV) in $h^{-1}$ was defined as follows:

GHSV=Inlet gas flow (g $h^{-1}$)/Weight of material (g)  Formula (3)

The $CH_4$ selectivity was defined as follows:

$S_{CH4}$ (%)=(Moles of $CH_4$ produced)/(1×Moles of $CO_2$ reacted)×100  Formula (4)

The selectivity of various products $S_c$ was defined as follows:

$S_c$ (%)=(C atoms in species i)/(C atoms produced in gas phase)×100  Formula (5)

where species i=$CH_4$, $CO_2$ and CO

The carbon balance was defined as follows:

Carbon balance (%)=($FC_{out}/FC_{in}$)×100  Formula (6)

where $FC_{in}$ and $FC_{out}$ are inlet and outlet molar flow rates (mol $h^{-1}$) of the reactants and products in the system.

EXAMPLE 3: Methane Production analysis: All catalysts synthesized in example 1 were evaluated for synthesis of methane w.r.t. various parameters including conversion of $CO_2$, selectivity of different products and yield of methane. The data is illustrated in table no. 3.

A) Using Single metal Oxides: The active metal so selected were Ni, Fe and Cu whereas the supports were selected as $Al_2O_3$, $CeO_2$ and $ZrO_2$. These studies were conducted in order to determine the best catalyst-support system that exhibits highest $CO_2$ conversion, highest $CH_4$ yield, selectivity and long-term stability. The catalysts were selected are as follows, Ni/$Al_2O_3$, Ni/$CeO_2$, Ni/$ZrO_2$, Fe/$Al_2O_3$, Fe/$CeO_2$, Cu/$Al_2O_3$ and Cu/$CeO_2$. The main reaction products formed during $CO_2$ hydrogenation are $CH_4$, CO and $H_2O$. No hydrocarbon compounds except methane were seen.

B) Mixed metal oxides: The present invention focuses on synthesis and application mixed metal oxide catalysts to combine the features of two active metals and supports for their synergistic effect to perform the dual role as active catalyst and stable support in a single system. Where, two metals have been combined along with two supports. Firstly, $CeO_2$ was selected as a common support whereas $Al_2O_3$ and $ZrO_2$ were the other supports. The supports were taken in the ratio of 3:1 where, $CeO_2$ was taken as 3. Similarly, Ni was selected as the common catalyst based on the previous literature. The other catalysts selected were Fe and Cu. The catalysts were selected are as follows: Ni—Fe/$CeO_2$—$Al_2O_3$, Ni—Cu/$CeO_2$—$Al_2O_3$, Ni—Fe/$CeO_2$—$ZrO_2$ and Ni—Cu/$CeO_2$—$ZrO_2$.

C) Novel alkali promoted mixed metal oxide catalyst-support Composition as per present invention: In this section, a novel catalyst-support system i.e. Cs—Ni—Fe/$CeO_2$-$\gamma Al_2O_3$ has been employed for enhanced and long-term production of $CH_4$. The synergistic effect of Ni and Fe ($NiFe_2O_4$) increased the dissociation and $CO_2$ hydrogenation, and weakened the C=O bond of $CO_2$ adsorbed on $CeO_2$-$\gamma Al_2O_3$ and Ni—Fe active sites.

The synergistic effect observed in earlier trial when catalyst composition having combination of support system comprising $CeO_2$—$Al_2O_3$ (3:2 mole ratio) and active metal combination of Ni—Fe (10% each) at 350° C. were clearly addressed.

The role of each metal in the system is important in influencing the overall performance of the catalyst. It was observed from the table that with 1000 h of reaction time, the conversion of $CO_2$ remained stable between 85 and 64%. This suggests that the reactant molecule shows effective and strong adsorption on catalyst sites resulting in very high conversion for longest period of time (1000 h). This novel synthesized Cs—Ni—Fe/$CeO_2$-$\gamma Al_2O_3$ catalyst composition also showed highest $CH_4$ selectivity (99-99.5%) and almost ~zero CO selectivity out of all synthesized catalysts so far.

TABLE 3

| Catalyst | Mole ratio of support | Reaction time (h) | Conversion of $CO_2$ (%) | Selectivity of $CH_4$ (%) | Selectivity of CO (%) | Yield of $CH_4$ (%) |
|---|---|---|---|---|---|---|
| Ni/$Al_2O_3$ | NA | 30 | 78.6 | 91.56 | 8.44 | 71.96 |
| Fe/$Al_2O_3$ | NA | 37 | 75.1 | 92 | 8 | 69.09 |
| Ni/$CeO_2$ | NA | 50 | 71.1 | 97.6 | 2.4 | 69.39 |

TABLE 3-continued

| Catalyst | Mole ratio of support | Reaction time (h) | Conversion of CO$_2$ (%) | Selectivity of CH$_4$ (%) | Selectivity of CO (%) | Yield of CH$_4$ (%) |
|---|---|---|---|---|---|---|
| Fe/CeO$_2$ | NA | 50 | 67.9 | 95.4 | 4.6 | 64.77 |
| Cu/Al$_2$O$_3$ | NA | 23 | 55.1 | 89.89 | 10.11 | 49.52 |
| Cu/CeO$_2$ | NA | 45 | 47.48 | 92.09 | 7.91 | 43.72 |
| Ni/ZrO$_2$ | NA | 8 | 33.6 | 96.2 | 3.8 | 32.32 |
| Ni—Cu/CeO$_2$-Al$_2$O$_3$ | (Ce-Al: 3:1) | 160 | 76.43 | 94.5 | 5.5 | 72.22 |
| Ni—Fe/CeO$_2$-ZrO$_2$ | (Ce-Zr: 3:1) | 140 | 70.71 | 91.5 | 8.5 | 64.69 |
| Ni—Cu/CeO$_2$-ZrO$_2$ (3:1) | (Ce-Zr: 3:1) | 100 | 54.38 | 83.3 | 16.7 | 45.29 |
| Ni—Fe/CeO$_2$-Al$_2$O$_3$ | (Ce-Al: 3:1) | 200 | 82.63 | 96.8 | 3.2 | 79.98 |
| Ni—Fe/CeO$_2$-Al$_2$O$_3$ | (Ce-Al: 1:1) | 150 | 65.8 | 97.3 | 2.7 | 64.02 |
| Ni—Fe/CeO$_2$-Al$_2$O$_3$ | (Ce-Al: 2:1) | 170 | 71.2 | 97.6 | 2.4 | 69.49 |
| Ni—Fe/CeO$_2$-Al$_2$O$_3$ | (Ce-Al: 3:2) | 200 | 85.4 | 99.1 | 0.9 | 84.43 |
| Cs-Ni—Fe/CeO$_2$-γAl$_2$O$_3$ | (Ce-Al: 3:2) | 1000 | 85-64 | 99-99.5 | 0.5-1 | 84.2-64.6 |

Catalyst composition: Single and mixed metal mixed catalysts for CO$_2$ methanation reaction.

Figure 1:
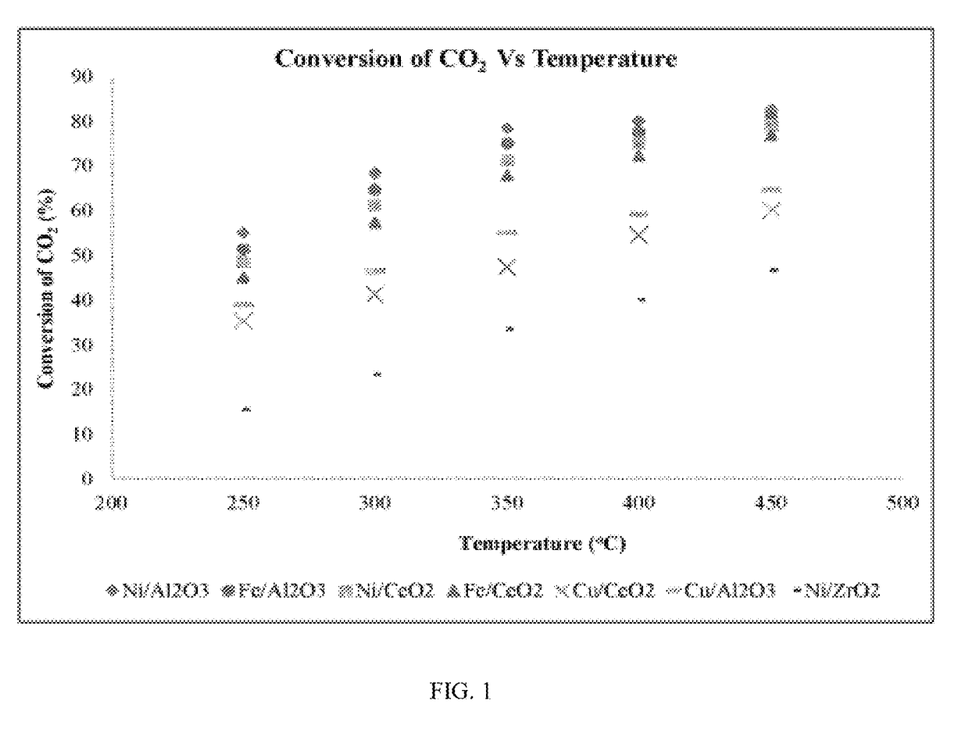
FIG. 1: Illustrates Effect of temperature on conversion of $CO_2$ for single metal oxide catalysts.

EXAMPLE 4: Effect of temperature on CO$_2$ conversion rate: To study the effect of temperature on reaction, it was desired to deduce the optimum temperature for maximum CO$_2$ conversion. Here, the temperature range selected for the study varied between 250-450° C. (FIG. 1). As seen from FIG. 1, for all catalysts, the conversion of CO$_2$ increased significantly from 250° C. to 350° C. Interestingly, the conversion increased slowly above 350 to 450° C. for all the catalysts. Between 350 and 450° C., the CO$_2$ conversion did not increase at the same rate as it rose from 250° C. to 350° C. which means that there is gradual increase in CO$_2$ conversion beyond 350° C. This pattern was observed for all single metal oxide catalysts. Thus, it was concluded that 350° C. was the optimum temperature to conduct CO$_2$ methanation reaction for all synthesized catalysts.

From FIG. 1, it was observed that amongst all catalysts, Ni/Al$_2$O$_3$ and Fe/Al$_2$O$_3$ exhibited the highest CO$_2$ conversion of 78.6 and 75.1%, respectively at 350° C. The conversion of CO$_2$ decreased in the following order of Ni/Al$_2$O$_3$ (max)>Fe/Al$_2$O$_3$>Ni/CeO$_2$>Fe/CeO$_2$>Cu/Al$_2$O$_3$>Cu/CeO$_2$>Ni/ZrO$_2$.

Figure 2:
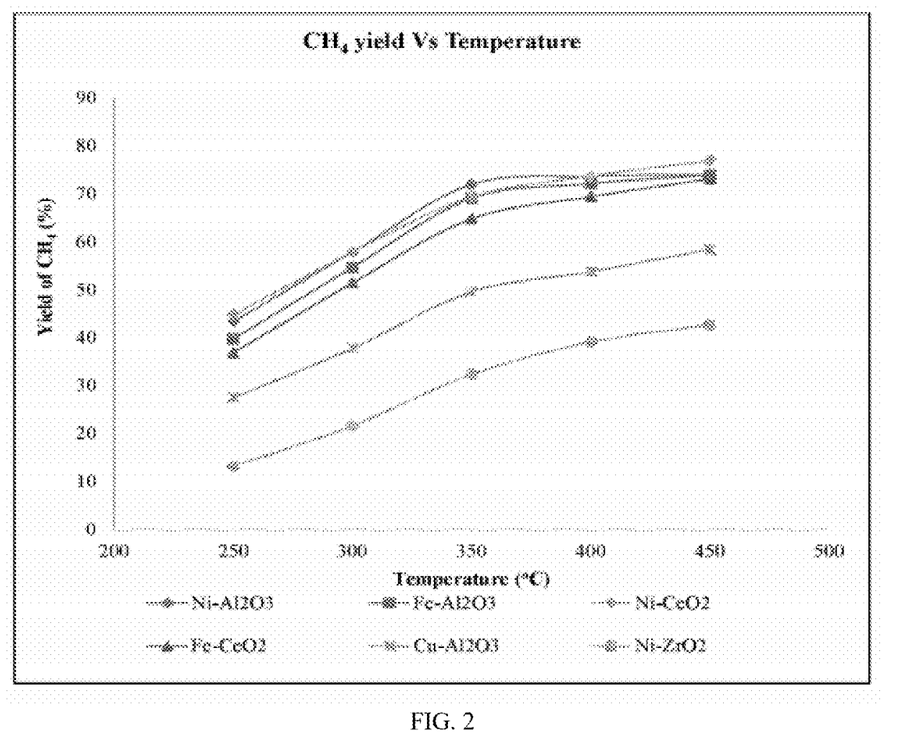
FIG. 2: Illustrates Yield of $CH_4$ for different single metal oxide catalysts at different temperature performed at reaction conditions: Catalyst weight: 3.0 g, $H_2$ flow rate: 30 ml/min, $CO_2$ flow rate: 21 ml/min, Pressure: 0.1 MPa.

From FIG. 2, it was observed that the yield of CH$_4$ increased as temperature increased from 250-450° C. for all investigated catalysts. Increasing temperature from 250-350° C. has a significant impact on higher yields of every studied single metal oxides but when temperature was raised from 350 to 450° C., no significant effect was observed on increasing yields of all the catalysts. Amongst all the catalysts, Ni and Fe based catalysts over Al$_2$O$_3$ support showed the highest CH$_4$ yields (71 and 69%, respectively) at 350° C. Ni and Fe based catalysts over CeO$_2$ support also showed high CH$_4$ yields (69 and 64%, respectively) at 350° C. At the same temperature, Cu based catalysts on Al$_2$O$_3$ and CeO$_2$ support showed comparatively low CH$_4$ yields of 49 and 43%, respectively. Ni/ZrO$_2$ catalyst has the lowest CH$_4$ yield of 32%. Hence, all single metal oxides were kept in the order of Ni/Al$_2$O$_3$ (max)>Fe/Al$_2$O$_3$>Ni/CeO$_2$>Fe/CeO$_2$>Cu/Al$_2$O$_3$>Cu/CeO$_2$>Ni/ZrO$_2$ for achieving high CH$_4$ yield.

Figure 3:
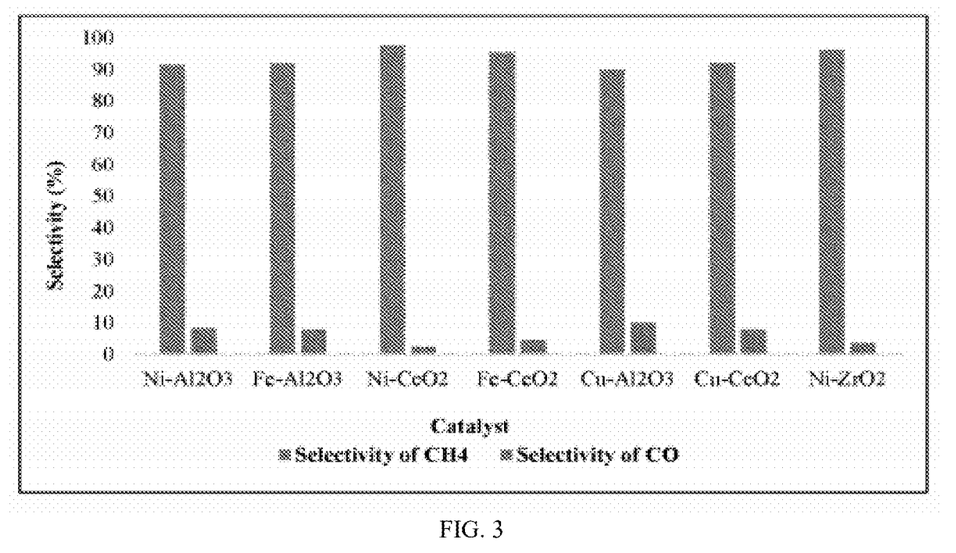
FIG. 3: Illustrates Selectivity profiles of $CH_4$ and CO for single metal oxide catalysts at 350° C. performed at reaction conditions: Catalyst weight: 3.0 g, temp: 350° C., $H_2$ flow rate: 30 ml/min, $CO_2$ flow rate: 21 ml/min, Pressure: 0.1 MPa.

From FIG. 3, it can be state that the superiority of single metal oxides in terms of high CH$_4$ and low CO selectivity for CO$_2$ methanation reaction is shown in the order of Ni/CeO$_2$ (max)>Ni/ZrO$_2$>Fe/CeO$_2$>Cu/CeO$_2$>Fe/Al$_2$O$_3$>Ni/Al$_2$O$_3$>Cu/Al$_2$O$_3$.

Figure 4:
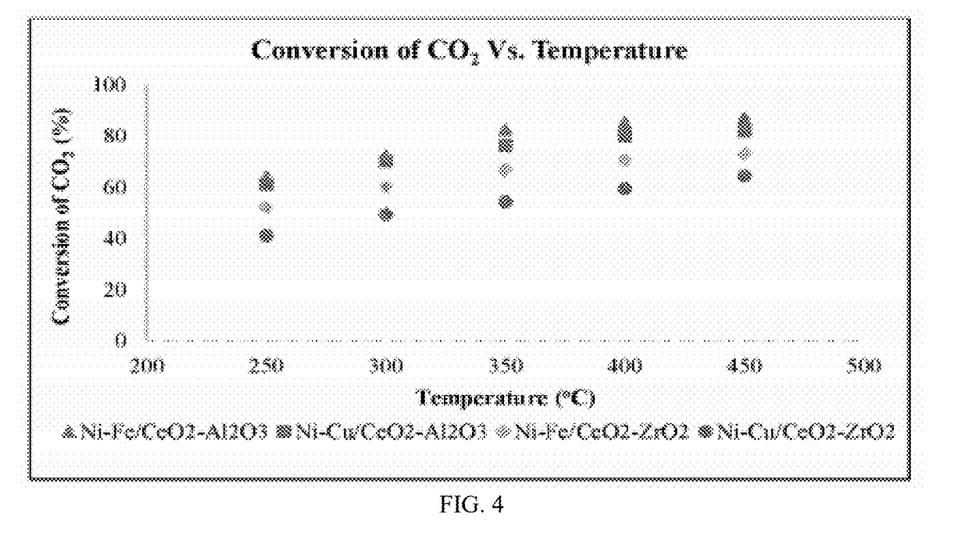
FIG. 4: Illustrates Effect of temperature on conversion of $CO_2$ for mixed metal oxide catalyst performed at reaction conditions: Catalyst weight: 3.0 g, $H_2$ flow rate: 30 ml/min, $CO_2$ flow rate: 21 ml/min, Pressure: 0.1 MPa.

From FIG. 4, it was observed that the catalyst composition comprising Ni—Fe/CeO$_2$-Al$_2$O$_3$ catalyst showed the maximum CO$_2$ conversion for all ranges of temperature studied, followed by Ni—Cu/CeO$_2$—Al$_2$O$_3$ catalyst. The enhanced activity may be explained by parallel contributions of an enhanced CO$_2$ adsorption by CeO$_2$—Al$_2$O$_3$ support and activation at the Ni and Fe species. At 350° C., CO$_2$ conversions were obtained in the following order of Ni—Fe/CeO$_2$—Al$_2$O$_3$ (82.63% max)>Ni—Cu/CeO$_2$—Al$_2$O$_3$ (76.43%)>Ni—Fe/CeO$_2$—ZrO$_2$ (66.71%)>Ni—Cu/CeO$_2$—ZrO$_2$ (54.38%). These results are encouraging as compared to single metal oxides reported in the first part of our study. The highest CO$_2$ conversion for single metal oxide, i.e. Ni/Al$_2$O$_3$ catalyst at 350° C. was obtained as 78.6% which is 4.03% lesser than Ni—Fe/CeO$_2$—Al$_2$O$_3$ catalyst. Such high conversion can be due to the synergistic effect of two metals with active and stable supports, uniform metal distribution for favourable metal-alloy formation, small crystallite size and high surface area resulting in better access to active sites of the catalyst. CeO$_2$—ZrO$_2$ support was the least active support in terms of CO$_2$ conversion than CeO$_2$-Al$_2$O$_3$ support. This may be since CeO$_2$ is basic and very stable support. Al$_2$O$_3$ support provided the highest activity (Ni/Al$_2$O$_3$) as we have seen in the case of single metal oxides. Hence combining CeO$_2$ with Al$_2$O$_3$ in 3:1 mole ratio was good approach for active and stable catalyst in single system. ZrO$_2$ is also a basic support and is not as active and thermally stable as Al$_2$O$_3$ support which was also proved in studies conducted in single metal oxides with Ni/ZrO$_2$ catalyst.

Figure 5:
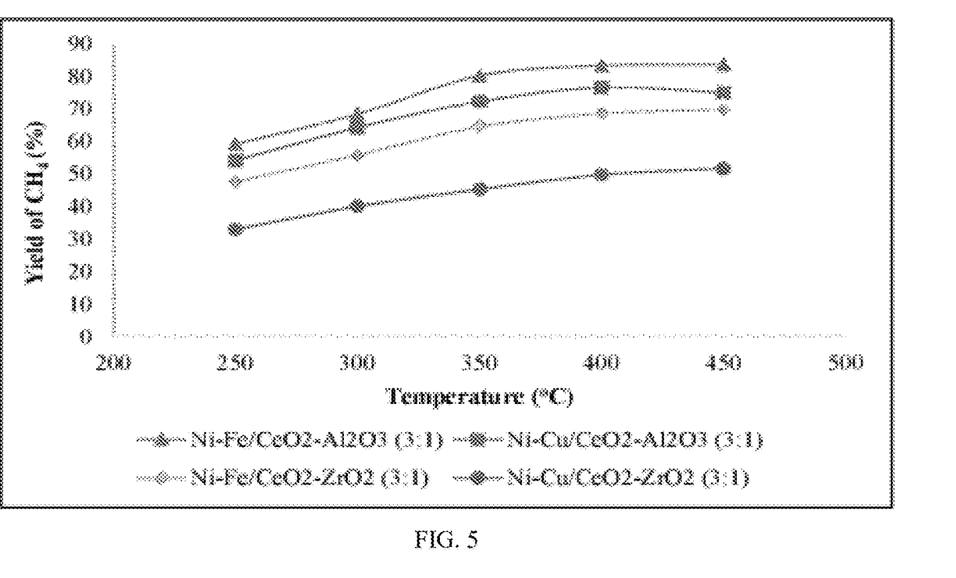
FIG. 5: Illustrates Yield of $CH_4$ for different mixed metal oxide catalysts at different temperature performed at reaction conditions: Catalyst weight: 3.0 g, $H_2$ flow rate: 30 ml/min, $CO_2$ flow rate: 21 ml/min, Pressure: 0.1 MPa.
Figure 6:
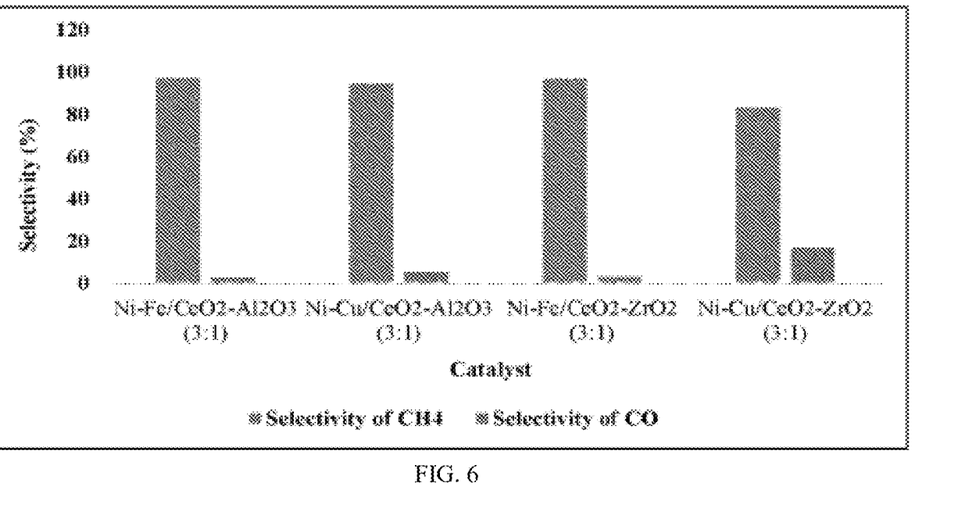
FIG. 6: Illustrates Selectivity profile of $CH_4$ and CO for mixed metal oxide catalysts at 350° C. performed at reaction conditions: Catalyst weight: 3.0 g, temp: 350° C., $H_2$ flow rate: 30 ml/min, $CO_2$ flow rate: 21 ml/min, Pressure: 0.1 MPa.

In order to study the effect of catalysts for the formation of various products, viz., CH$_4$ and CO, studies were conducted between 25° and 450° C. to assess their selectivity and yield. The rates of CH$_4$ and CO formation at 250, 300, 350, 400 and 450° C. were found to be 92, 94, 97, 97, 95 and 7, 5, 2, 2, 4, respectively for Ni—Fe/CeO$_2$-Al$_2$O$_3$ catalyst, 88, 91, 94, 95, 91 and 11, 8, 5, 4, 8, respectively for Ni—Cu/CeO$_2$—Al$_2$O$_3$ catalyst, 91, 92, 96, 97, 95 and 8, 7, 3, 2, 4, respectively for Ni—Fe/CeO$_2$—ZrO$_2$ catalyst and 80, 81, 83, 83, 80 and 19, 18, 16, 16, 19, respectively for Ni—Cu/CeO$_2$—ZrO$_2$ catalyst. As can be seen from the results, for all above mixed oxides, CH$_4$ selectivity increases steadily with temperature up to 400° C., post which (450° C.) it begins to decrease due to rise in CO formation. Out of all, Ni—Fe/CeO$_2$—Al$_2$O$_3$ provided the lowest CO formation (2.8 and 2.3% for 350 and 400° C., respectively) particularly due to the addition of CeO$_2$ in Al$_2$O$_3$ which helps to increase the surface area, reducing the nickel and iron oxide's grain size, better resistance to carbon deposition, stronger thermo-stability, and lower reduction temperature. This catalyst-support system gave the highest CH$_4$ selectivity and the lowest CO formation. In terms of yields of CH$_4$, a similar effect is seen for all four mixed oxide catalysts with highest yields obtained at temperatures between 350 (80%) and 400° C. (83%) for Ni—Fe/CeO$_2$-Al$_2$O$_3$ catalyst. CH$_4$ yields for other three catalysts, viz., Ni—Cu/CeO$_2$—Al$_2$O$_3$, Ni—Fe/CeO$_2$—ZrO$_2$ and Ni—Cu/CeO$_2$ at 350° C. were 72, 64 and 45%, respectively and 76, 68 and 49% for 400° C., respectively (FIGS. 5 and 6).

Figure 7:
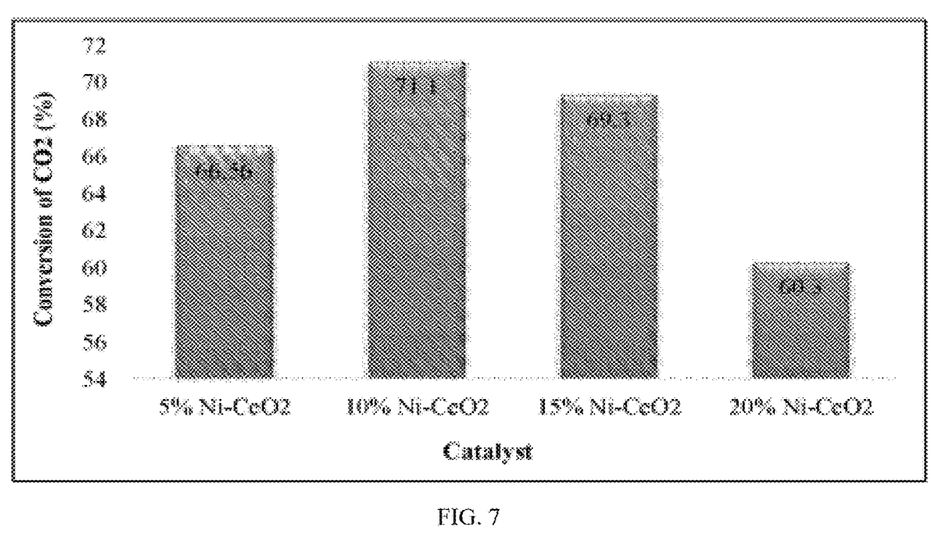
FIG. 7: Illustrates Effect of different nickel loading over Ni—$CeO_2$ support on conversion of $CO_2$ to $CH_4$ performed at reaction conditions: Catalyst weight: 3.0 g, temp: 350° C., $H_2$ flow rate: 30 ml/min, $CO_2$ flow rate: 21 ml/min, Pressure: 0.1 MPa.

EXAMPLE 5: Effect of nickel loading on $CO_2$ conversion: It was also important to determine the optimum Ni loading to be used as an active metal in the catalyst for maximum $CO_2$ conversion. Out of many single metal oxide catalysts studied, Ni/$CeO_2$ catalyst was selected to study the effect of nickel loading on $CO_2$ conversion. The reason of choice of Ni/$CeO_2$ catalyst for this study out of various single metal oxides is that it showed good conversion and highest stability of 50 h for $CO_2$ methanation reaction. Various Ni loadings such as 5, 10, 15 and 20 wt. % were studied at 350° C., over $CeO_2$ support (FIG. 7). It was found that as the loading of Ni increased the $CO_2$ conversion also rose. The maximum conversion was obtained at 10 wt. % (71.1%) and 15 wt. % (73.3%) of metal loading which could be attributed to better dispersion and access to the active sites. As can be seen from FIG. 7, there is no substantial increase in the rate of $CO_2$ conversion from 10 wt. % to 15 wt. %. Only 2% increase in $CO_2$ conversion was observed with 5 wt. % addition in 10 wt. % Ni/$CeO_2$ catalyst which looks uneconomical. A significant increase in $CO_2$ conversion (21%) was observed when Ni loading was increased from 5 wt. % to 10 wt. %. In contrast to this, as we increased metal loading from 15 wt. %-20 wt. %, a sudden drop in the $CO_2$ conversion was noticed. This may be due to the fact that increasing active metal loading above optimum level forms aggregate or agglomerates on support surface. This leads to increase in metal particle and crystallite sizes. Increasing crystallite sizes of the active metal decreases its dispersion over the support which leads to blockage of surface-active sites on the catalyst surface which are primarily responsible for adsorption and activation of the reactants. The catalytic activity is the rate of reaction. In the case of well dispersed catalysts, reaction rate is proportional to the catalytic sites exposed, but when the dispersion of active sites on a support surface gets affected owing to the increase in metal crystallite sizes due to agglomerates formation then catalytic activity also decreases. Anything that alters the environment in the vicinity of catalytic active sites can alter its activity.

EXAMPLE 6: Time on stream studies (TOS) to check long term stability of catalyst: The studies to assess the long-term stability by the way of conversion of $CO_2$ for the selected catalyst-support system was performed at 350° C., as can be seen, different catalysts showed different conversions at the same reaction temperature (350° C.).

Figure 8:
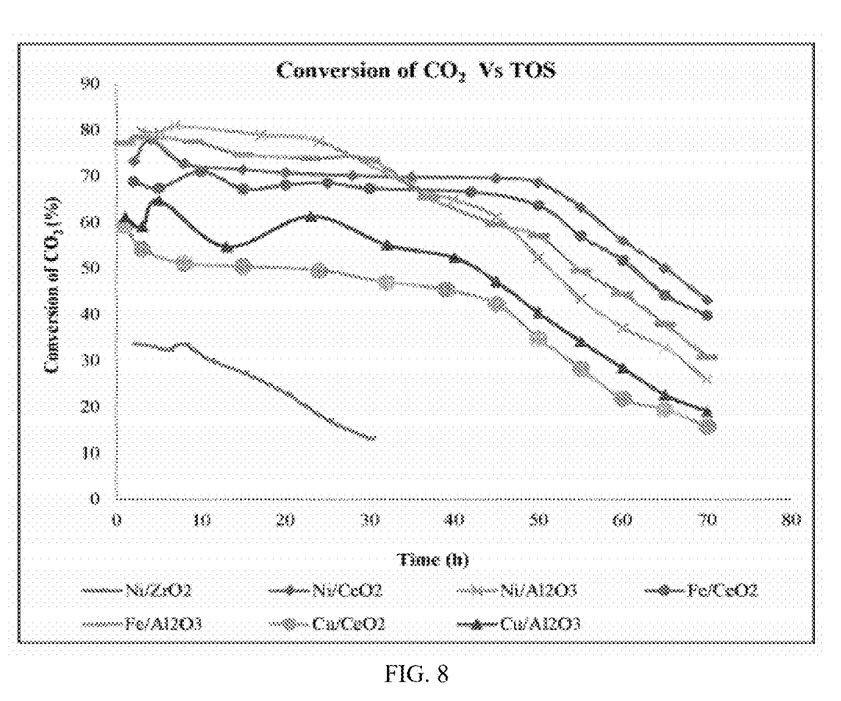
FIG. 8: Illustrates Time on stream study of single metal oxide catalysts for conversion of $CO_2$ to $CH_4$ performed at reaction conditions: Catalyst weight: 3.0 g, temp: 350° C., $H_2$ flow rate: 30 ml/min, $CO_2$ flow rate: 21 ml/min, Pressure: 0.1 MPa.

From FIG. 8, particularly, all metals with $CeO_2$ as support showed higher stability (>40 h) by exhibiting similar $CO_2$ conversions for longer period of time in comparison with $Al_2O_3$ (30 h) and $ZrO_2$ (8 h) supported catalysts. This behaviour of $CeO_2$ based catalysts can be attributed to the fact that Ce is known to increase the thermal stability of the material and assist in inhibiting formation of carbon thus increasing longevity of the catalyst. Alumina supported catalyst such as Ni/$Al_2O_3$ and Fe/$Al_2O_3$ showed highest conversion up to 30 h. After 30 h. of reaction time, a substantial decrease in $CO_2$ conversion for alumina supported catalysts was observed. The Fe/$Al_2O_3$ catalyst showed slightly better stability than Ni/$Al_2O_3$ catalyst. Though its conversion was slightly less than Ni/$Al_2O_3$ catalyst up to 45 h of reaction time, but after 45 h, the conversion of Fe/$Al_2O_3$ catalyst was observed higher than Ni/$Al_2O_3$ catalyst and remained higher up to 70 h. This behaviour of Fe/$Al_2O_3$ catalyst is due to the fact that Fe is very popular Fischer-Tropsch (F-T) catalyst which can efficiently adsorb CO on its active sites and convert it into $CH_4$. Cu based catalyst did not show more attractive results as its conversion (55 and 47% for Cu/$Al_2O_3$ and Cu/$CeO_2$, respectively) and stability (23 and 42 h for Cu/$Al_2O_3$ and Cu/$CeO_2$, respectively) was comparatively much lower than Ni and Fe based catalysts. A Ni/$ZrO_2$ catalyst was noted as least favourable catalyst in terms of conversion (33%) and stability (only up to 8 h). Amongst all catalysts, Ni/$CeO_2$ showed the best performance for TOS studies with similar $CO_2$ conversions (>65%) up to 50 h., followed by Fe/$CeO_2$ catalyst (>63%) for nearly 50 h. The stability of the single metal oxides is depicted in the following decreasing order of Ni/$CeO_2$ (50 h. max)~Fe/$CeO_2$ (50 h. max)>Cu/$CeO_2$ (45 h.)>Fe/$Al_2O_3$ (37 h.)>Ni/$Al_2O_3$ (30 h.)>Cu/$Al_2O_3$ (23 h.)>Ni/$ZrO_2$ (8 h.).

Figure 9:
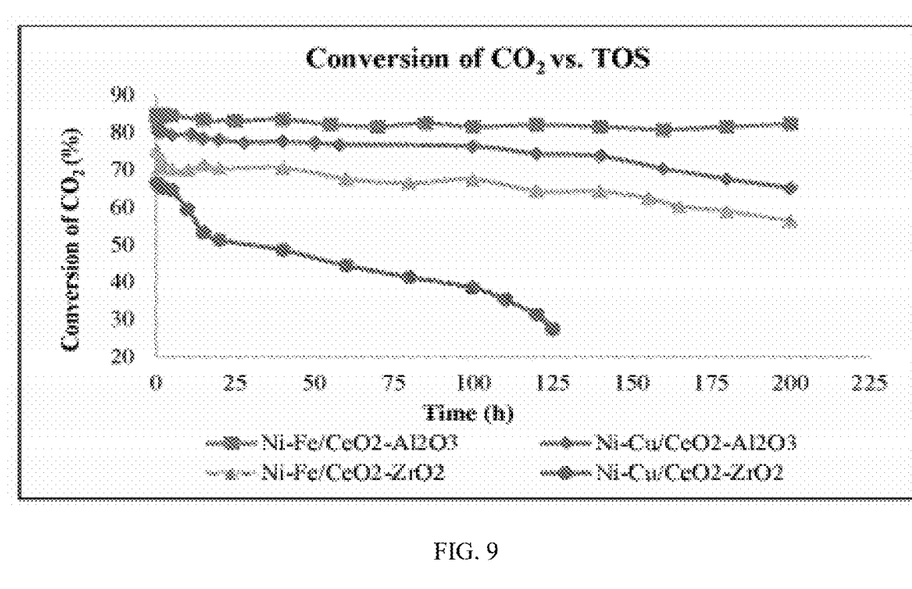
FIG. 9: Illustrates Time on stream study of mixed metal oxide catalysts for conversion of $CO_2$ to $CH_4$ performed at reaction conditions: Catalyst weight: 3.0 g, temp: 350° C., $H_2$ flow rate: 30 ml/min, $CO_2$ flow rate: 21 ml/min, Pressure: 0.1 MPa.
Figure 12:
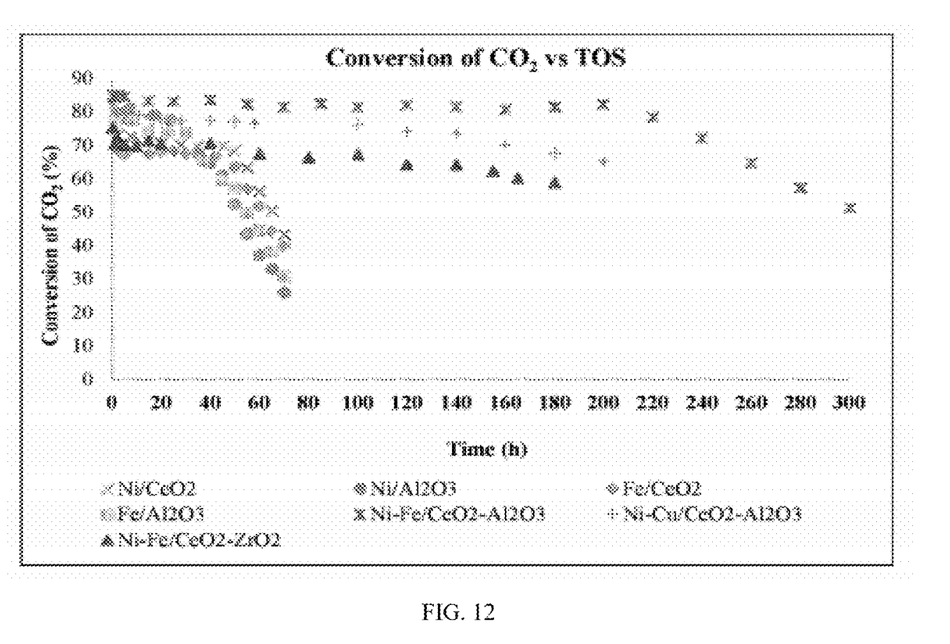
FIG. 12: Illustrates comparison of support system on Time on stream study.

As can be seen FIG. 9 and FIG. 12, different catalysts showed different conversions and time stabilities at the same reaction temperature. Particularly, the Ni and Fe based catalysts with $CeO_2$ and $Al_2O_3$ as support (Ni—Fe/$CeO_2$—$Al_2O_3$) showed long term stability of up to 200 h. reporting similar conversions throughout. The $CO_2$ conversion of Ni—Fe/$CeO_2$—$Al_2O_3$ catalyst at 5 min and 200 h was found to be 84 and 82%, respectively. Only 2% decrease in $CO_2$ conversion was seen up to 200 h. No other catalyst has given such a stable conversion for long period of time. The reason behind highly active and stable catalyst is mainly combination of $CeO_2$-$Al_2O_3$ support. Ceria, as one of the most important rare earth oxides, can absorb and release oxygen via the transformation between $Ce^{3+}$ and $Ce^{4+}$. For this reason, it has been widely used as active component in many catalytic reactions for increasing stability. Ceria has been employed as structural and electronic promoter to improve the performance of Ni and Fe based catalysts. Ceria could not only improve the thermal stability of $Al_2O_3$, but also promote the dispersion of metal Ni and Fe on the support. Ni—Cu/$CeO_2$—$Al_2O_3$ and Ni—Fe/$CeO_2$—$ZrO_2$ catalyst were stable up to 160 and 140 h., respectively. A Ni—Cu/$CeO_2$—$ZrO_2$ catalyst exhibited highest conversion of 64.6% at 5 mins of reaction time and continuously decreased thereafter up to 25 h. (51.2%). At 125 h. of reaction time, only 27% $CO_2$ conversion was obtained for Ni—Cu/$CeO_2$—$ZrO_2$ catalyst which proved its inefficiency as active and stable catalyst for $CO_2$ methanation reaction.

Figure 11:
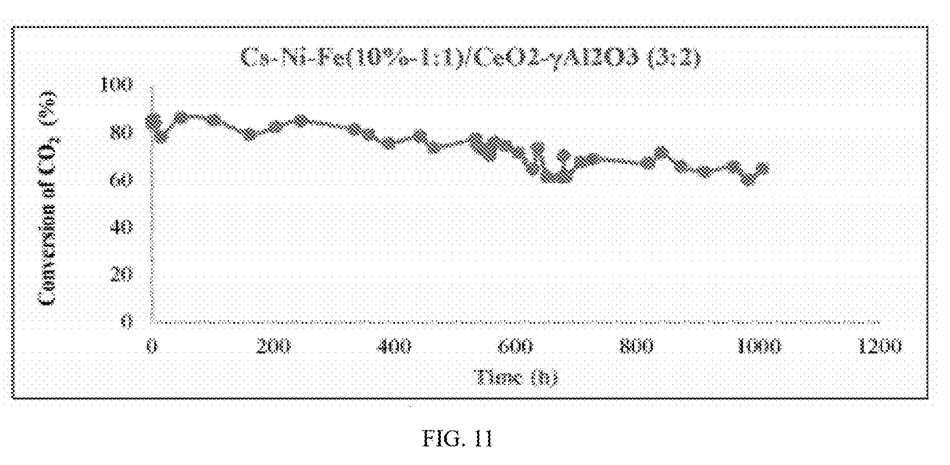
FIG. 11: Illustrates Time on stream study of novel Cs—Ni—Fe/$CeO_2$-$\gamma Al_2O_3$ catalyst for conversion of $CO_2$ to $CH_4$ performed at reaction conditions: Catalyst weight: 3.0 g, temperature: 350° C., $H_2$ flow rate: 30 ml/min, $CO_2$ flow rate: 21 ml/min, Pressure: 0.1 MPa.
Figure 13:
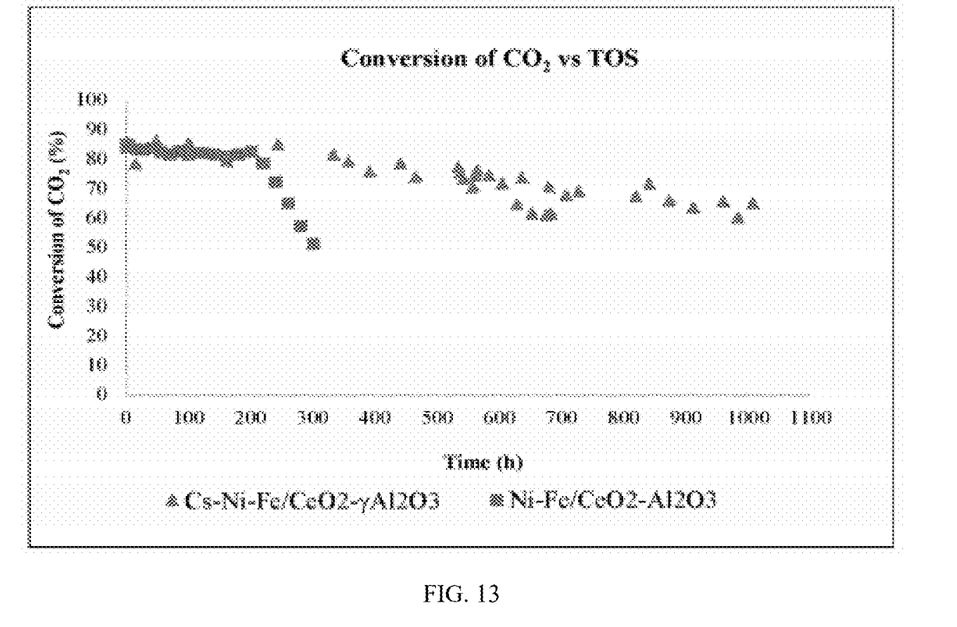
FIG. 13: Illustrates comparison of with and without alkali promoted metal and with and without $\gamma Al_2O_3$ effect on Time on stream study as per present invention.

As per inventive step of present invention, the role of each metal in the system is important in influencing the overall performance of the catalyst. It was observed from the FIG. 11 and FIG. 13 that, the conversion of $CO_2$ remained stable for up to 1000 h, whereas the catalyst devoid of alkali promoter Cs, conversion of $CO_2$ dropping after 200 h and reached 50% within 300 h (FIG. 13). Furthermore, up to 1000 h of reaction time, the conversion of $CO_2$ remained stable between 85 and 64%. This suggests that the reactant molecule shows effective and strong adsorption on catalyst sites resulting in very high conversion for longest period of time (1000 h.). This novel synthesized Cs—Ni—Fe/$CeO_2$-$\gamma Al_2O_3$ catalyst composition also showed highest $CH_4$ selectivity (99-99.5%) and almost ~zero CO selectivity out of all synthesized catalysts so far.

CO poisoning, one of the worst catalyst deactivating processes, is a crucial issue especially for all metal catalysts in $CO_2$ methanation process. During $CO_2$ dissociation step to CO via RWGS reaction or direct dissociation, adsorbed CO molecules generated as reaction intermediates and hinder the reaction by blocking the catalysts active sites if CO does not convert further into $CH_4$ and comes out in outlet gas stream. Hence CO methanation is called as a rate determining step in $CO_2$ methanation reaction. Cesium promoted Ni—Fe/$CeO_2$-$\gamma Al_2O_3$ catalyst-support system was designed and developed for this particular reaction such that almost ~100% $CH_4$ and ~zero CO selectivity was obtained which helped this catalyst to showcase very long term stability (1000 h.) by mitigating CO poisoning effect over the catalysts. No other catalyst showed such a low CO concentration in their outlet gas stream than this novel synthesized catalyst which limits its long-term stability. The synergistic effect of Ni and Fe, highly selective and active support ($CeO_2$-$\gamma Al_2O_3$, respectively) and alkali promoter like Cs in single catalyst made this catalyst highly active, selective and stable for more than 100 h. There are many reasons for very high activity, selectivity, and stability of this newly synthesized Cs—Ni—Fe/$CeO_2$-$\gamma Al_2O_3$ catalyst which are illustrated in reaction mechanism part.

Figure 10:
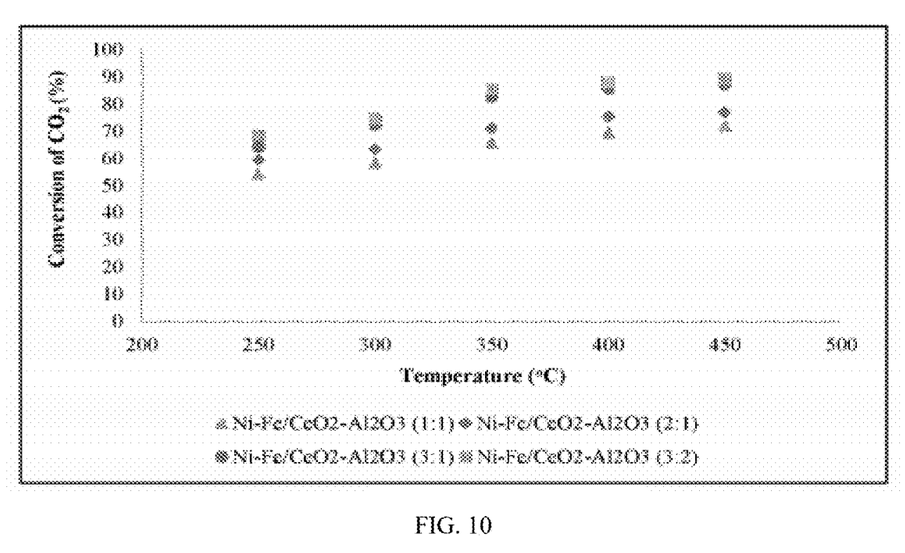
FIG. 10: Illustrates Effect mole ratio of $CeO_2$—$Al_2O_3$ on conversion of $CO_2$ to $CH_4$ performed at Reaction conditions: Catalyst weight: 3.0 g, $H_2$ flow rate: 30 ml/min, $CO_2$ flow rate: 21 ml/min, Pressure: 0.1 MPa.

EXAMPLE 7: Effect of combination of $CeO_2$-$Al_2O_3$ mole ratio in catalyst support system on $CO_2$ conversion: It was desired to determine the optimum mole ratio of $CeO_2$-$Al_2O_3$ by studying the effect of various ratios on $CO_2$ conversion. Ni—Fe/$CeO_2$-$Al_2O_3$ were evaluated at different mole ratios of $CeO_2$-$Al_2O_3$ such as 1:1, 2:1, 3:1 and 3:2 at various temperatures ranging from 250-450° C. As observed from the FIG. 10, as the ratio of $CeO_2$ increased from 1 to 3, the conversion of $CO_2$ also rose for all temperatures. As can be seen from FIG. 4 regarding effect of temperature, highest $CO_2$ conversion was obtained at 350 and 400° C., wherein conversions rose from 65.8% (350° C.) at 1:1 ($CeO_2$—$Al_2O_3$) to 85.4% (350° C.) at 3:2 ($CeO_2$—$Al_2O_3$) mole ratios. This shows that the higher amounts of $CeO_2$ contributed to better catalyst activity due to its redox properties owing to the $Ce^{3+}$ and $Ce^{4+}$ ions. The addition of Ce to Al decreased the selectivity of CO which is a by-product at the same time. Also the addition of $CeO_2$ did not block more pores or decrease the surface area and the pore volume of the catalysts. It may result from the effect of the added Ce increasing the surface area of the catalyst by increasing active metals dispersion. In addition, $Al_2O_3$ used at mole ratio of 2 showed better catalytic activity with $CeO_2$ due to the high mechanical strength of $Al_2O_3$. So a conclusion can be drawn that the addition of $Al_2O_3$ over $CeO_2$ support with the mole ratio of Al:Ce (1:3 and 2:3) can bring the overall performance of the catalyst by enhancing the mechanical strength and resistance to the impact of carbon deposition, respectively.

Post these temperatures, there is no substantial increase in $CO_2$ conversion and thus, it is economical and obvious to operate at 350° C. and 3:2 mole ratios ($CeO_2$—$Al_2O_3$) for obtaining maximum $CO_2$ conversion.

Therefore, the important objective and aim of present intention was to enhance the activity of the Ni—Fe/$CeO_2$—$Al_2O_3$ catalyst for very long period (>1000 h.), lower formation of intermediates and stronger resistance to coke formation for achieving highest selectivity for $CH_4$. Based on earlier findings mentioned in the earlier section, the present inventors synthesized a novel combination of cesium promoted Ni—Fe catalyst over $CeO_2$-$\gamma Al_2O_3$ support which is abbreviated as Cs—Ni—Fe/$CeO_2$-$\gamma Al_2O_3$ catalyst having long term stability in synthesis of methane gas. The foregoing description of the invention has been set merely to illustrate the invention and is not intended to be limiting. Since modifications of the disclosed embodiments incorporating the spirit and substance of the invention may occur to person skilled in the art, the invention should be construed to include everything within the scope of the disclosure.

We claim:

1. A heterogeneous catalyst for selective carbon dioxide methanation reaction having high activity and long-term stability (>1000 hours), the catalyst comprising of:
   at least one alkali promoter metal,
   two active metals and
   support for active metals having combination of $CeO_2$-$\gamma Al_2O_3$, wherein the heterogeneous catalyst has a surface area between 200 and 800 ($m^2/g$), pore volume between 0.5 and 2.5 ($cm^3/g$) and average pore diameter between 5 and 30 nm.

2. The heterogeneous catalyst for selective carbon dioxide methanation reaction as claimed in claim 1, wherein the alkali promoter metal is Cesium.

3. The heterogeneous catalyst for selective carbon dioxide methanation reaction as claimed in claim 1, wherein the concentration of alkali promoter metal is between 1 and 5 wt. % on the basis of total weight of the support.

4. The heterogeneous catalyst for selective carbon dioxide methanation reaction as claimed in claim 1, wherein the active metals are Nickel and Iron.

5. The heterogeneous catalyst for selective carbon dioxide methanation reaction as claimed in claim 1, wherein the concentration of active metals is between 5 and 20 wt. % on basis of total weight of the support combination.

6. The heterogeneous catalyst for selective carbon dioxide methanation reaction as claimed in claim 1, wherein the mole ratio of the support combination of $CeO_2$-$\gamma Al_2O_3$ is selected as 3:2.

7. A process for preparation of heterogeneous catalyst for selective carbon dioxide methanation reaction as claimed in claim 1 comprising:
   step 1) drop-wise addition of nickel nitrate, iron nitrate and cesium nitrate to an aqueous solution mixture of cerium nitrate and aluminum nitrate at continuous stirring rate and temperature at 363 K;
   step 2) simultaneously, dropwise addition of $Na_2CO_3$ to the step 1) solution and maintaining alkaline pH between 9-10 by the addition of 2M NaOH solution;
   step 3) precipitating out the reaction mixture at 443 K for 24 h in Teflon lining bomb reactor (pressure vessel) for hydrothermal treatment;
   step 4) cooling the solution to room temperature and separation of precipitate by filtration;
   step 5) washing of precipitate with de-ionized water for several times to attain neutral pH;
   step 6) drying of precipitate at 383 K for 12 h; and
   step 7) calcination of dried precipitate at temperature 973 K for 5 h in air atmosphere.

* * * * *